United States Patent [19]

Hoge

[11] 4,009,075
[45] Feb. 22, 1977

[54] PROCESS FOR MAKING ALCOHOL FROM CELLULOSIC MATERIAL USING PLURAL FERMENTS

[75] Inventor: William H. Hoge, Flemington, N.J.

[73] Assignee: Bio-Industries, Inc., Hialeah, Fla.

[22] Filed: Aug. 22, 1975

[21] Appl. No.: 606,789

[52] U.S. Cl. .............................. 195/33; 195/111; 195/115
[51] Int. Cl.$^2$ ..................................... C12C 11/14
[58] Field of Search ............... 195/33, 13, 37, 39, 195/40, 41, 90, 94, 91, 82, 111, 34, 113, 119, 116, 124, 125, 115; 426/11, 13, 14, 9; 210/11, 2, 3

[56] References Cited

UNITED STATES PATENTS

| 1,443,881 | 1/1923 | Langwell | 195/33 |
|---|---|---|---|
| 1,639,571 | 8/1927 | Langwell | 195/119 |
| 2,893,919 | 7/1959 | Opderbeck et al. | 195/39 |
| 3,764,475 | 10/1973 | Mandels et al. | 195/33 |
| 3,845,218 | 10/1974 | Mussell | 195/37 X |

FOREIGN PATENTS OR APPLICATIONS

| 316,719 | 12/1971 | U.S.S.R. | 426/13 |
|---|---|---|---|

OTHER PUBLICATIONS

Raitseua, "Control methods for continuous alcohol fermentation of hydrolyzates", *Chemical Abstracts* vol. 67, abs. No. 31531m, p. 2962, (1967).

Drublyanets, et al., "Use of organic matter in wood hydrolyzates, removed with steam by microorganisms", *Chemical Abstracts* vol. 74, abs. No. 86328a, p. 307 (1971).

Converse et al., "Acid hydrolysis of cellulose in refuse to sugar and its fermentation to alcohol," *Chemical Abstracts*, vol. 79, abs. No. 124663u, p. 270, (1973).

Polovinkin, "Indexes of wood hydrolysis dependent on the time of year", *Chemical Abstracts* vol. 75 abs. No. 38096x, p. 105, (1971).

*Primary Examiner*—A. Louis Monacell
*Assistant Examiner*—Thomas G. Wiseman
*Attorney, Agent, or Firm*—Folsom E. Drummond

[57] ABSTRACT

A process for making alcohol from cellulosic material by hydrolyzing the material to sugars and subjecting the resultant reaction mixture to digestion and fermentation to convert the sugars to alcohol. The process comprises sterilization of the cellulosic material; concurrent digestion and fermentation of the sterilized mixture to produce alcohol using innoculum comprising cellulase enzyme and yeast, vacuum stripping to recover the alcohol, and recovery of innoculum for reuse.

9 Claims, No Drawings

PROCESS FOR MAKING ALCOHOL FROM CELLULOSIC MATERIAL USING PLURAL FERMENTS

THE INVENTION

This invention relates to a process of making alcohol from cellulosic material. The process is particularly applicable to the production of ethyl alcohol or ethanol from cellulosic fibers of waste materials.

It is, of course, well known that ethyl alcohol is produced by fermentation of sugars by yeasts. Alcoholic beverages are made by the enzymatic digestion of starches to form sugars, and the subsequent fermentation of the sugars by yeasts to form alcohol. The production of alcohol from the acid hydrolysis of cellulosic material such as wood, and the fermentation of the resulting sugar to alcohol has been known for more than 50 years, but in recent years this approach has not been competitive.

Alcohol is now produced commercially by several synthetic processes, including, for example, the treatment of unsaturated hydrocarbons under high pressure with a mixture of carbon monoxide and hydrogen in the presence of a catalyst. These prior processes for producing alcohol depend on ample supplies of petroleum hydrocarbons and the continuity of these supplies is no longer certain.

Alcohol forms a useful fuel and may be utilized in admixture with other fuels, for example, gasoline to produce a low cost fuel. Ethyl alcohol, as produced from cellulosic waste materials in accordance with the present invention, also is useful as a solvent; extractant; antifreeze; intermediate in the synthesis of innumerable organic chemicals, and as an essential ingredient of alcoholic beverages and pharmaceuticals.

Whereas, recent processes have been described for the conversion of cellulose to simple sugars by enzymatic hydrolysis, e.g. U.S. Pat. Nos. 3,642,580 and 3,764,475, no efficient method for producing alcohol from cellulosic materials at relatively low cost as compared with prior known methods has been developed. The present invention provides such a process.

The process of this invention comprises essentially three steps which may be outlined as follows:

1. Sterilization
    Cellulose fiber-containing material, such as waste, is subjected to a steam-treatment sufficiently to eliminate unwanted bacterial strains which later may cause unwanted reactions. Thereafter the resultant sterilized mass is adjusted to the proper solids content, temperature and pH for effective fermentation reactions;
2. Concurrent digestion and fermentation
    The cellulosic fiber mass of step (1) is reduced to fermentable sugars by innoculation and fermentation of the mass with yeast and enzymes, e.g. cellulase, to produce alcohol;
3. Alcohol removal
    The alcohol formed by step (2) is removed as by stripping, e.g. vacuum distillation; the yeasts and enzymes are then recycled for reuse.

Improvement features of this inventive process of making alcohol from cellulosic materials include, for example:
    I. The use of non-proteolytic yeasts to ferment sugars in conjunction with vacuum distillation removal of carbon dioxide and ethyl alcohol in the same reaction vat with the enzymatic hydrolysis of the cellulose to sugars, and thereby obtain the following desirable results;
        a. Elimination of large volumes of cooling water, such as normally required to control the temperature of fermentation. In processes heretofore known, it is typical to use 50 to 80 gallons of cooling water per gallon of alcohol, whereas the present process uses practically none;
        b. The removal of the reaction products may be carried out in a continuous or intermittent manner in order to force the reactions to completion. Sugar formed by the enzymatic breakdown of the cellulose is immediately removed when it is fermented by the yeasts. The alcohol formed by the fermentation of the sugars is likewise continuously removed by the vacuum distillation.
        c. The bottoms or solution which remains after the sugar and alcohol production is completed will still retain active cellulase enzyme and yeasts, and this innoculum solution, therefore, may be recycled to dilute new quantities of incoming sterilized cellulosic fibers.
    II. In the embodiment wherein mineral acid is used in the sterilizer in combination with enzymatic hydrolysis in the later fermentation step, a reduction in the reaction time and the sizes of the tanks or vats is realized over the non-acid hydrolysis embodiment. The initial acid sterilization treatment is carried out a high solids content, e.g. 25 to 40% by weight, and which results in a partial breakdown of the individual fibers to form a more fragmented fiber structure which is more accessible to subsequent enzymatic hydrolysis. Fibers sterilized in the presence of acid can be slurried at higher solids content than is possible with fibers sterilized with steam alone. For example, acid sterilized fiber can be slurried at 8 to 12% solids, forming an easily stirred mixture, whereas if the acid is not used the solids must be reduced to about 5% for comparable ease of stirring. The use of the higher fiber concentrations reduces tank sizes and aids reaction speeds.
    III. By combining the sterilization with partial acid hydrolysis the maximum benefit with respect to the cost of this treatment step is obtained. Further, steam sterilization is needed to eliminate unwanted bacterial strains, as hereinbefore explained, and the acid treatment causes the cellulose degradation to get started during this treatment step which otherwise would not bring about substantially complete degradation of the cellulose fibers in the same reaction times.
    IV. Utilization of yeasts having the capability of producing ethyl alcohol from the sugars formed during the process is, of course, a prerequisite to obtaining the best results.

The following examples are illustrative but not limitative of the present invention; the parts and percentages given are by weight unless otherwise stated:

EXAMPLE I

Approximately 100 grams (dry weight) of fibrous cellulosic material, such as recovered from a municipal waste slurry after being dewatered in a filter press, and which resultant mass comprises a total solids content of about 38% and less than 20% of non-fibrous material, is subjected to a sterilizing treatment. To accomplish this, the fibrous material is placed in a 1-liter stainless steel pressure vessel or container fitted with a pressure gage and steam inlet line for the introduction of high pressure steam. Non-condensable gasses, e.g. air, etc., first are removed from the fibrous material being treated by heating the container e.g. in an oil bath to a temperature of about 90° C. for 10 to 15 minutes while the steam inlet line remains open to permit the gasses to escape. High pressure saturated steam is then injected into the container until the pressure gage indicates about 140 psi. This steam pressure is maintained for approximately 15 minutes after which the steam line is shut off and the container is allowed to cool to room temperature. To shorten the cooling time, the container is immersed in a steam of cold water.

Following sterilization, the fibrous mass of material is transferred from the container to a jacketed vacuum vessel equipped with a 40 rpm stirrer, the vessel being connected to a pump to maintain a vacuum of about 26 inches of Hg in the vessel. The sterilized fibrous mass is diluted to a total volume of approximately 2 liters by the addition of 400 ml (milliliters) of innoculum solution, as hereinafter described, and 1.2 liters of sterile water. The innoculum solution consists of two primary components, although minor amounts of other compatible substances which do not prevent microbial growth may be present. The primary component is cellulase enzyme culture broth as prepared by the action of *Trichoderma viride* on cellulose as described, for example, in U.S. Pat. No. 3,764,475 aforementioned. The second component of the innoculum solution is a non-proteolytic yeast which converts simple sugars to ethanol. An example of such yeast is *Saccharomyces cerevisiae* var. *ellipsoideus*, as described, for example, in various publications originating from the Cornell University, Department of Chemical Engineering. The culture which contains 0.3 to 1.0 mg of protein/ml is adjusted to a pH of 4.5 by the addition of oleic acid and other nutrients commonly used in such yeast fermentations. (A pH range of 3.0 to 5.0 is permissible.)

The allowable temperature in the jacketed vessel which the cellulase can tolerate is 55° C without damage, whereas yeasts have maximum temperatures of 30° to 45° C. *Saccharomyces cerevisiae* can withstand only about 30° C. Accordingly, the innoculated fibrous cellulose material in the jacketed vessel is maintained at a temperature of 30° C under mild agitation. The reaction is permitted to proceed for about eight hours with periodic application of vacuum as needed to avoid the temperatures above about 30° C which might kill the yeast. After about 16 hours the reaction is essentially completed as judged by the fact that it is no longer necessary to apply vacuum to prevent the temperature from rising above 30° C. During the reaction the vapor phase material is removed from the jacketed vessel and condensed to form a liquid condensate which is distilled to recover a yield of about 25 ml of 95% ethyl alcohol. The removal of the alcohol at this relatively low temperature permits recycling and reuse of the non-volatile portion of the reaction mixture to replace dilution water and to reduce the amount of innoculum needed for the next batch. This non-volatile portion contains yeast, cellulase enzyme and unreacted materials. Where desired, the culture or non-volatile portion of the reaction mixture may be concentrated by ultrafiltration as commonly practiced.

The process may be carried out as a continuous or intermittent procedure, products formed throughout the process being removed to force the reaction to completion. Likewise, the alcohol produced during the fermentation is removed continuously or intermittently by the vacuum treatment.

EXAMPLE II

The process as described in Example I is repeated using a sterilizing cellulosic mixture consisting of 100 grams of dry fiber and 163 grams of water and 5 ml of 10% sulfuric acid. The resulting slurry mixture after sterilization is treated with slaked lime to raise the pH to 4.5. The resultant mixture forms a more fluid mass than the sterilized mixture of Example I, and is diluted with 0.6 liters of water and 0.4 liters of innoculum solution as described in Example I. This provides a total volume of one liter, which mixture is easily stirred with the 40 rpm agitator. The presence of the acid in the sterilization treatment serves to permit a higher solids content of the fibrous slurry mass and this increases the enzyme concentration during the fermentation step which results in increasing the productivity of the fermentation.

EXAMPLE III

The fibrous cellulosic material is sterilized by treatment with steam as described in Example I. Four different batches of 100 grams each (dry weight) are prepared and stored under sterile conditions for later use. The first 100 gram batch of fibrous mass is then transferred to the jacketed vacuum vessel. The dilution and the addition of innoculum solution follows the procedure of Example I. The vacuum is only used intermittently to prevent the temperature from exceeding the effective temperature range for the fermentation of the sugars. After twelve hours the effective viscosity of the fibrous slurry is greatly reduced by the action of the enzymes. The vessel is opened and the second 100 gram (dry weight) batch of fibrous mass is added to the partially digested fiber from the first batch. The solids content of the second batch, as it is added to the reaction vessel, is 20 to 30%, having been diluted only by the steam used in the sterilizing step. In the same manner, the third batch of fibrous mass is added 24 hours after the addition of the first batch, and the fourth batch of fibrous mass is added 36 hours after the addition of the first batch. At the end of the 48th hour the vacuum on the vessel is increased to 35 mm Hg and the alcohol vapors are removed at a temperature of 30° C and collected as described in Example I.

The additions of successive additions of sterilized fibrous mass to the previously started innoculated fibrous reaction mixture offers a convenient modification of the system for recycling the enzymes and yeasts. In Examples I and II the recycled enzymes and yeasts are added to new batches of sterilized fibrous mass, whereas in Example III the new batches of sterilized fibrous mass are added to the previously used enzymes and yeasts.

Various systems for removing and purifying the alcohol can be used with the invention. For example, the process for removing the alcohol can be modified by using ternary azeotropic mixtures which permit the use of lower vacuums (e.g. 300 mm Hg). An example of such a ternary mixture is the system hexane-ethanol-water and the use of this system is well known to those skilled in the art. In this system hexane is added to the alcohol-containing reaction mixture at the end of the 48-hour period and the vapors contain the ternary mixture which is then separated into its components by decantation and distillation.

Various microbiological systems for fermenting the sugars to form alcohol can be used with this invention. For example, certain strains of bacteria are known to produce alcohol from sugars. The agent which is responsible for the formation of the alcohol must not interfere with the cellulase digestion of the fibrous cellulose.

The innoculum solution will contain nutrients and two primary ingredients, as previously stated. These primary ingredients are cellulase enzyme and the yeast or yeast-substitute. The innoculum will also contain secondary ingredients. For example, if the fibrous material originates from garbage where there is a significant non-cellulosic carbohydrate fraction, e.g. starches, it is desirable to include small quantities of alpha-amylase and glucoamylase enzymes which are commonly used in the processing of corn starches. If the fibrous material is woody material with a high lignin content, e.g. sawdust, it is desirable to include lignin-attacking agents such as the pleitropic mutants of the wood-rotting fungus *Polyporus adustus*, described in Canadian Journal of Microbiology, 20 (1974) 371–378.

An important feature of this invention which provides a lower cost process for producing ethanol from cellulosic fibrous material, as compared with prior art known processes, is the provision of steam sterilization with or without the presence of acid in the fibrous mass. When acid is included, a neutralizing agent, such as lime or the like alkali is added to increase the pH of the mixture, as described. Another improvement feature of the invention comprises concurrent digestion of the cellulase enzyme to form simple sugars, such as glucose, and fermentation of the sugars to produce ethanol with the continuous or intermittent removal of the alcohol to prevent temperature buildup. The inventive process additionally provides for retention of the enzyme and yeast of the innoculum solution in the form suitable for recycling and reuse in a subsequent batch or with additional cellulosic material subsequently added to the original batch.

What is claimed is:

1. A process for making ethanol from cellulosic fibrous material comprising the steps of steam sterilization of the cellulosic material, thereafter subjecting the resultant sterilized cellulosic material to digestion and fermentation reaction with an innoculum mixture comprising cellulase enzyme and a yeast whereby the cellulosic material is converted to simple sugars with conversion of said sugars to ethanol and recovering ethanol from said digestion and fermentation reaction by vacuum stripping, and recycling the innoculum enzyme-containing residual liquid for reuse to digest subsequent charges of cellulosic material, said digestion of the cellulosic material to simple sugars and the fermentation reaction of the sugars to ethanol being carried out concurrently.

2. The process according to claim 1 wherein the digestion of the cellulosic material to sugars, the fermentation of the sugars to alcohol and the vacuum stripping of the alcohol are carried out simultaneously.

3. The process according to claim 1 wherein the vacuum stripping of the alcohol from the reacted fibrous material is used to maintain temperatures below 45° C.

4. The process according to claim 1 wherein the innoculum mixture comprises cellulase enzyme and non-proteolytic yeast.

5. The process according to claim 1 wherein the innoculum mixture comprises cellulase enzyme, non-proteolytic yeasts and one or more materials selected from the group consisting of alpha-amylase, glucoamylase and lignin-attacking agents.

6. The process according to claim 1 wherein the recycling of the innoculum is accomplished by successive additions of sterilized fibrous material to innoculated fibrous material which has undergone previous reaction.

7. The process according to claim 1 wherein the sterilized cellulosic material comprises a cellulosic slurry of sulfuric acid and partially degraded cellulose.

8. The process according to claim 7 wherein the cellulosic slurry is neutralized by the addition of alkali to adjust the pH of the mixture.

9. The process according to claim 4 wherein the non-proteolytic yeast is *Saccharomyces cerevisiae, and the cellulase enzyme comprises a culture broth of Trichoderma viride.*

* * * * *